United States Patent [19]

Jacobsen, Jr. et al.

[11] Patent Number: 5,600,241
[45] Date of Patent: Feb. 4, 1997

[54] VIBRATING-REED SUSCEPTOMETER FOR MEASURING ANISOTROPIC ASPECTS OF SUSCEPTIBILITY

[75] Inventors: Ronald L. Jacobsen, Jr., London, Ohio; Alexander C. Ehrlich, Alexandria, Va.

[73] Assignee: The United States of America as Represented by the Secretary of the Navy, Washington, D.C.

[21] Appl. No.: 499,527

[22] Filed: Jul. 7, 1995

[51] Int. Cl.⁶ .......................... G01N 27/72; G01R 33/02
[52] U.S. Cl. ........................................... 324/228; 324/259
[58] Field of Search ...................... 324/228, 234, 324/236, 201, 256–262

[56] References Cited

U.S. PATENT DOCUMENTS

| | | | |
|---|---|---|---|
| 3,904,956 | 9/1975 | O'Brien et al. | 324/228 |
| 4,037,149 | 9/1977 | Foner | 324/228 X |
| 4,861,990 | 8/1989 | Coley | 324/201 X |
| 5,001,426 | 3/1991 | Frey et al. | 324/259 |
| 5,015,953 | 5/1991 | Ferguson et al. | 324/244 |
| 5,252,920 | 10/1993 | Date et al. | 324/201 X |
| 5,311,125 | 5/1994 | Krause et al. | 324/201 |
| 5,369,980 | 12/1994 | Kocache | 324/204 X |

OTHER PUBLICATIONS

H. Drulis, et al., Phys. Rev. B 44, 4731 (1991).
W. Roos, et al., Rev. Sci. Instrum. 51, 612 (1980).
P. Monceau in *Electronic Properties of Inorganic Quasi–One–Dimensional Compounds, Part II: Experimental;* edited by P. Monceau (Reidel, Boston, 1985) p. 148.
P. L. Gammel, et al., Phys. Rev. Lett. 61, 1666 (1988).
S. Foner, Rev. Sci. Instrum. 30, 548 (1959).
R. P. Giffard, R. A. Webb, and J. C. Wheatley, J.Low Temp. Phys. 6, 533 (1972).
H. Zijlstra, Rev. Sci. Instrum. 41, 1241 (1970).
R. Reeves, J. Phys. E 5, 547 (1972).
M. J. Naughton, Doctoral thesis, Boston University, 1986.
T. Tiedje, R. R. Haering, and W. N. Hardy, J. Acoust. Soc. Am. 65, 1171 (1979).
X.-D. Xiang, J. W. Brill, and W. L. Fuqua, Rev. Sci. Instrum. 60, 3035 (1989).
S. Hoen, et al., Synthetic Metals 41–43, 3863 (1991).

*Primary Examiner*—Sandra L. O'Shea
*Assistant Examiner*—Roger Phillips
*Attorney, Agent, or Firm*—Thomas E. McDonnell; Chester L. Jordan

[57] ABSTRACT

A method for determining the anisotropy of the magnetic susceptibility of a sample includes determining the resonant frequency of the sample in substantially zero magnetic field, the resonant frequency being for flexure vibration in a selected plane of vibration. A second step is applying a uniform dc magnetic field to the sample, the magnetic field having a component in the selected plane of vibration. A third step is determining the resonant frequency of the sample in the presence of the applied magnetic field, the resonant frequency being for flexure vibration in the selected plane. The fourth step is determining the anisotropy of the magnetic susceptibility of the sample, based on the amplitude of the magnetic field component and on the above-determined resonant frequencies.

10 Claims, 3 Drawing Sheets

VIBRATING-REED SUSCEPTOMETER FOR MEASURING ANISOTROPIC ASPECTS OF SUSCEPTIBILITY

FIELD OF THE INVENTION

This invention relates generally to measurement of magnetic susceptibility, and more particularly to measurement of anisotropic aspects of magnetic susceptibility.

BACKGROUND OF THE INVENTION

The magnetic susceptibility of a sample describes the relation between an applied magnetic field H and the magnetization M induced in the sample by the magnetic field. The differential volume susceptibility $\chi$ is defined as $$\chi = \frac{\delta \vec{M}}{\delta \vec{H}}. \tag{1}$$

Since the applied magnetic field H and the magnetization M (magnetic moment per unit volume) are vectors, the susceptibility $\chi$ is most generally a second-rank tensor, especially for anisotropic materials. For diamagnetic, paramagnetic or antiferromagnetic material, the magnetization M is linearly related to the applied magnetic field H as $$\vec{M} = \chi \cdot \vec{H}, \tag{2}$$

where the largest components of the susceptibility tensor $\chi$ are typically on the order of $10^{-5}$. For such materials, the susceptibility tensor $\chi$ does not depend on the applied magnetic field H and the susceptibility has the same value as the differential susceptibility.

Magnetometers can be used to measure susceptibility by applying a known magnetic field to a sample and measuring the induced magnetic moment. They can also be used to measure differential susceptibility.

In a vibrating sample magnetometer, the sample is mounted on a support which is vibrated in a known magnetic field, thereby electromagnetically inducing voltage in a detection coil. See, S. Foner, "Versatile and Sensitive Vibrating-Sample Magnetometer," Rev. Sci. Instrum. 30, 548 (1959). The amplitude of the induced signal is considered to be a measure of the sample's magnetic moment and, therefore, susceptibility. As such a system measures magnetization by the effect of the sample on the current in a detection coil, it is limited in sensitivity by the noise and other limiting characteristics of the coil and its associated electronics. Such a system does not become more sensitive as the size of the specimen decreases and is not as effective as the size of the specimen decreases.

The frequency of vibration in a vibrating sample magnetometer is determined by the driving system and is not affected by properties of the sample. Furthermore, the test sample is mounted on a support, which may have a magnetization of its own, and thus a nulling procedure is used to subtract this effect. As the sensitivity of the vibrating sample magnetometer cannot readily be calculated a priori, such a system is typically calibrated against a known standard.

A vibrating sample magnetometer does not directly measure anisotropic aspects of susceptibility. In order to determine the difference between two components of susceptibility, the two components are first measured and then compared. Since the difference may be orders of magnitude smaller than the components themselves, such an indirect technique may introduce significant errors in measuring anisotropic aspects of susceptibility.

Force magnetometers measure a sample's magnetic moment by measuring the magnetic force exerted on the sample by an applied nonhomogeneous magnetic field. There are difficulties with producing the optimum nonhomogeneous magnetic field. One type of force magnetometer is a vibrating reed magnetometer, in which the sample is mounted on a flexible support. The sample mounted on the support is driven by an ac magnetic field at the flexible support's mechanical resonant frequency, and the flexible support provides a restoring mechanical force. The amplitude of vibration is considered proportional to the sample's magnetic moment. See, H. Zijlstra, "A Vibrating Reed Magnetometer for Microscopic Particles," Rev. Sci. Instrum. 41, 1241 (1970); W. Roos, "High Sensitivity Vibrating Reed Magnetometer," Rev Sci. Instrum. 51(5), 612 (1980). This technique has the same shortcomings as those discussed above for the vibrating sample magnetometer. It does not become more sensitive as the size of the specimen decreases and is not as effective as the size of the specimen decreases. It does not directly measure anisotropic aspects of susceptibility. Furthermore, because the vibrating reed magnetometer uses an external support which might affect the magnetization results, a nulling or subtraction procedure is used with such a system.

Vibrating reed experiments which measure changes in the resonant frequency of flexural resonance have been used to study the dynamics of superconductors. However, such experiments are related to flux line pinning and are not sensitive to anisotropic aspects of the sample's magnetic susceptibility. Such experiments do not measure anisotropic aspects of a sample's inherent magnetic susceptibility.

SUMMARY OF THE INVENTION

It is an object of this invention to directly measure anisotropic aspects of susceptibility.

It is another object of this invention to accurately measure anisotropic aspects of susceptibility of small samples or of samples with small susceptibility.

It is another object of this invention to accurately measure anisotropic aspects of susceptibility of a sample based on mechanical properties of the sample by the sample providing a mechanical restoring force.

It is a further object of this invention to measure anisotropic aspects of susceptibility using a uniform applied magnetic field.

The above objects can be accomplished by a method for determining the anisotropy of the magnetic susceptibility of a sample including determining the resonant frequency of the sample in substantially zero magnetic field, the resonant frequency being for flexure vibration in a selected plane of vibration. A second step is applying a uniform dc magnetic field to the sample, the magnetic field having a component in the selected plane of vibration. A third step is determining the resonant frequency of the sample in the presence of the applied magnetic field, the resonant frequency being for flexure vibration in the selected plane. The fourth step is determining the anisotropy of the magnetic susceptibility of the sample based on the amplitude of the magnetic field component and on the above-determined resonant frequencies.

The system so described directly measures the anisotropy of the susceptibility and thus provides more accurate measurements than indirect techniques, such as force magnetometers and vibrating sample magnetometers.

As the measurement is made on smaller and smaller samples, the magnetic force becomes smaller but the restoring mechanical force also becomes smaller and is not disproportionally greater than the smaller magnetic force. The dimensions of the sample can be optimally selected for measuring anisotropic aspects of susceptibility. Therefore, this invention accurately measures anisotropic aspects of susceptibility of small samples or of samples with small susceptibility. Because this system does not use an external support, it need not be calibrated against a known standard and does not require nulling or subtraction.

These and other objects, features and advantages of the present invention are described in or apparent from the following detailed description of preferred embodiments.

BRIEF DESCRIPTION OF THE DRAWINGS

The preferred embodiments will be described with reference to the drawings, in which like elements have been denoted throughout by like reference numerals, and wherein.

DETAILED DESCRIPTION OF THE PREFERRED EMBODIMENTS

Figure 1:
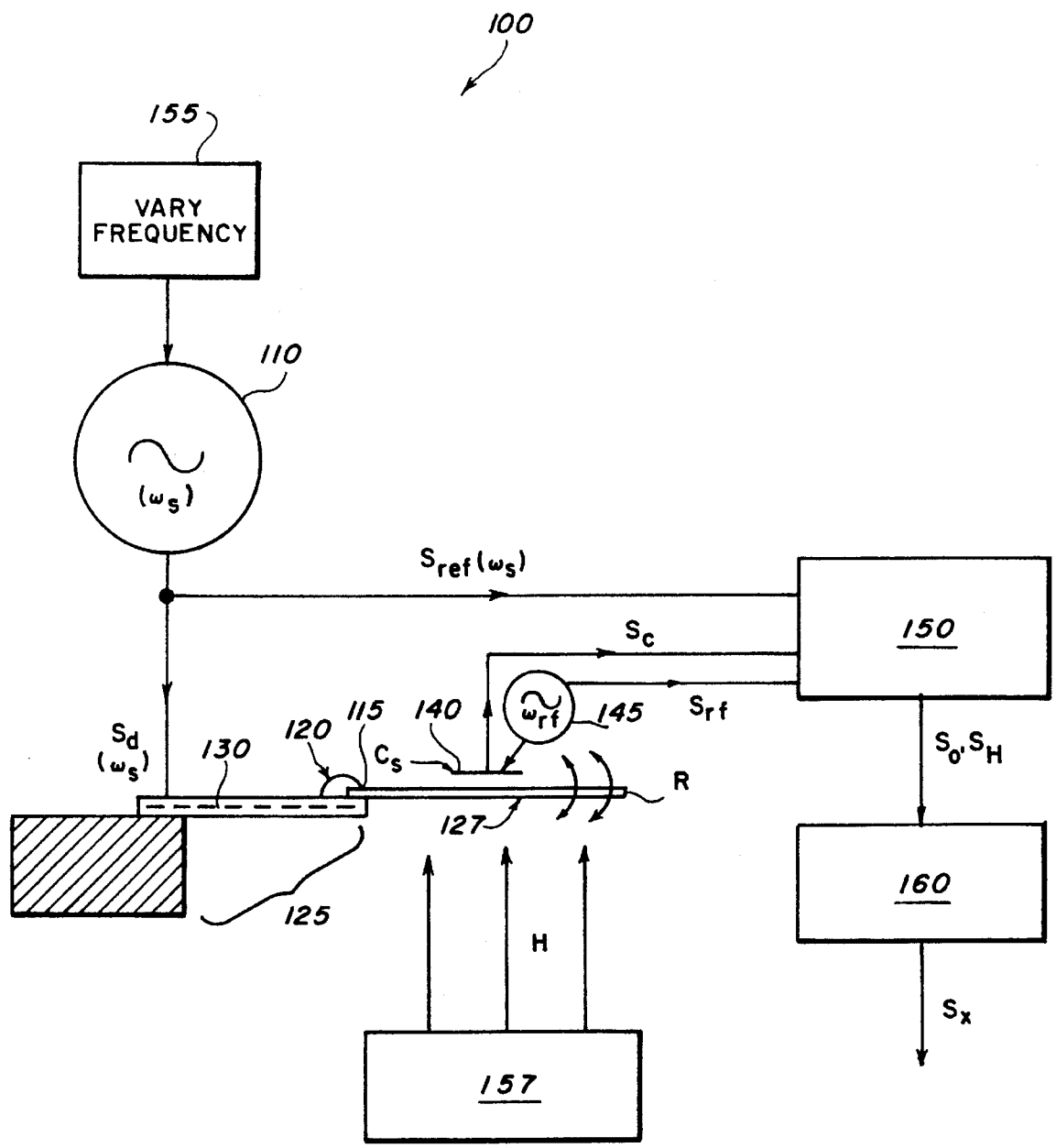
FIG. 1 shows in schematic form the operation of this invention.

Referring now to the drawings, FIG. 1 shows a system 100 for determining the anisotropy of the susceptibility of a sample R by measuring the effect of an applied magnetic field H on the sample's resonant frequency.

The sample R to be measured is a reed, defined as a mechanical member for which the primary restoring force against flexural distortion is provided by a modulus or stiffness of the member. Depending on the particular material and the context of measurement, the reed may be a bar, fiber, whisker, or platelet and is not restricted to single component reeds. Exemplary materials are carbon fibers (type GY-70 by Celion Carbon Fibers, BASF Structural Materials, Inc., 11501 Steele Creek Rd., POB 7687, Charlotte, N.C. 28241), NbSe$_3$ crystals, and thin copper wire. As a further example, the sample R could be a ferromagnetic thin film deposited on a weakly magnetic substrate reed. The invention could then be used to measure the anisotropy of susceptibility of such a sample R.

The resonant frequency of the sample R in a selected plane of vibration, for example the plane of FIG. 1, is first determined in the absence of applied magnetic field H, i.e. in substantially zero field. More specifically, the resonant frequency is determined for a selected mode of flexural vibration, for example, the fundamental mode, and for a given set of boundary conditions, such as vibration of a reed clamped at one end and free to vibrate at the other end. Examples of techniques known in the art for determining the resonant frequency for flexural vibration may be found in X.-D. Xiang et al., "Use of Helical Resonator as a Capacitive Transducer in Vibrating Reed Measurements," Rev. Sci Instrum. 60, 3035 (1989). and T. Tiedje et al., "The Application of Capacitive Transducers to Sound Velocity Measurements in TJF-TCNQ," J. Acoust. Soc. Am. 65, 1171 (1979), which articles are incorporated herein by reference.

As shown in FIG. 1, the resonant frequency of the sample R can be determined by using a drive oscillator 110 to produce a drive ac signal $S_d$ and a reference ac signal $S_{ref}$, each having angular frequency $\omega_s$, preferably in the range of about $2\pi \cdot 100$ radians/sec (rad/s) $-2\pi \cdot 100{,}000$ rad/s. An exemplary drive oscillator 110 is an HP3325A.

The sample R is attached at one end 115, for example by silver paint 120, to a fixed support 125. The other end 127 of the sample R is free to vibrate. Ideally, the ambient pressure is kept low in the vicinity of the reed by a vacuum system (not shown). A transducer responsive to the drive signal $S_d$ drives the sample R in flexural vibration at angular frequency $\omega_s$. A preferred transducer is a piezoelectric transducer 130, such as a series bimorph 130 (by Vernitron, Inc., Bedford, Ohio), which deflects when a voltage is applied to it, analogous to the way a bimetallic strip deflects upon application of heat. Strictly speaking, the sample end 115 moves with the transducer 130 and is not precisely fixed. However, the effect of the transducer's vibration on the analysis herein is negligible and so the sample end 115 will be considered fixed.

An alternative form of transducer is an electrostatic transducer (not shown). In this case, a small electrode carrying the drive voltage $S_d$ is brought near the reed S, preferably closer to the free end 127. This electrode and the reed R form two surfaces of a capacitor, and the voltage applied will exert a force tending to pull the two surfaces toward each other, thereby driving vibration of the reed S.

Figure 2:
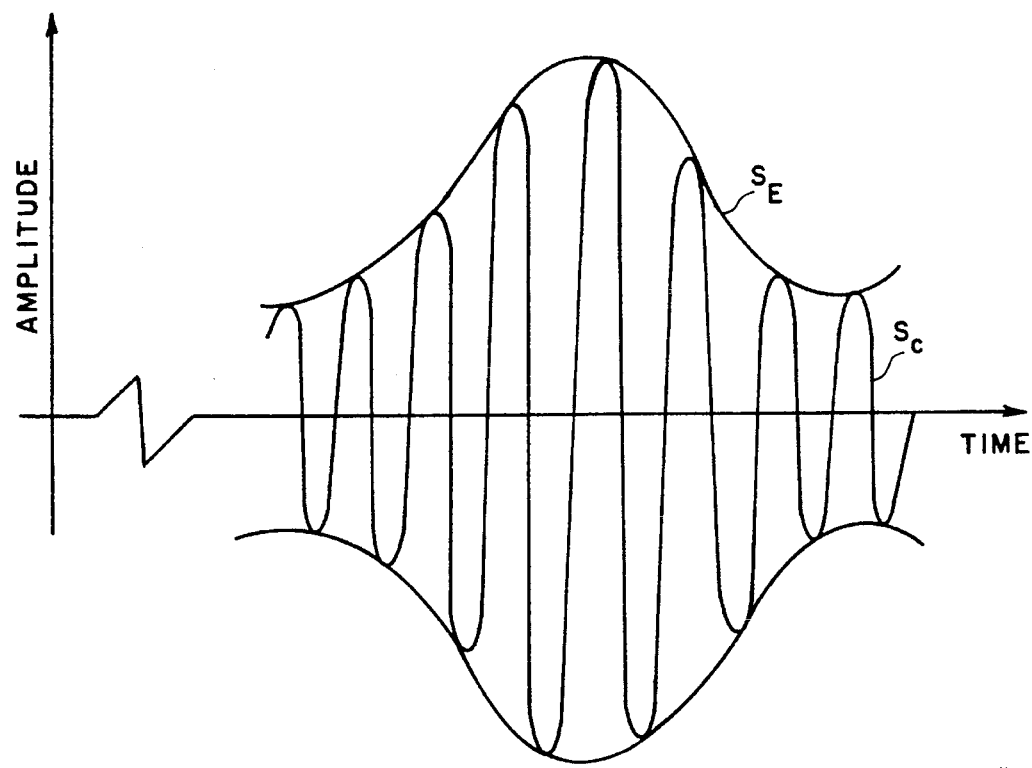
FIG. 2 is a graph of the time varying signals $S_c$ and $S_E$.

The motion of the sample R is then detected, preferably by capacitive detection means. Exemplary capacitive detection techniques are described in Xiang et al., supra, and T. Tiedje et al., supra. Such techniques are based on the capacitance $C_s$ between the sample R and a fixed member 140, for example, a plate or the open end of a helical resonator detection coil (not shown). That capacitance $C_s$ varies with time as the sample R vibrates: the capacitance $C_s$ is higher as the sample R is closer to the fixed member 140 and lower as the sample is farther from the fixed member 140. The capacitance $C_s$ is typically on the order of $10^{-19}$ Farads (F). An rf signal generator 145 generates and applies to the coil a carrier signal with angular frequency $\omega_{rf}$ appropriate for the apparatus and sample R. For example, the carrier frequency $\omega_{rf}$ could be on the order of $2\pi \cdot 450 \cdot 10^6$ rad/s. The level of signal in the coil is input to the analyzer 150 as capacitance signal $S_c$. Referring now to FIG. 2, this capacitance signal $S_c$ has the waveform of the carrier signal of angular frequency $\omega_{rf}$ amplitude modulated by a modulation signal of angular frequency $\omega_s$. Referring now to FIGS. 1 and 2, the analyzer 150 responsive to the capacitance signal $C_s$ and a reference signal $S_{rf}$ of angular frequency $\omega_{rf}$ isolates the envelope of the capacitance signal $C_s$ and produces a signal $S_E$ which is essentially a trace of the time-varying motion of the sample S. The analyzer 150 further analyzes the envelope signal $S_E$ to determine the amplitude of vibration $A(\omega_s)$ for this drive frequency $\omega_s$.

The angular frequency $\omega_s$ of the drive and reference signals, $S_d$ and $S_{ref}$ respectively, is selectively varied by a frequency controller 155. The analyzer 150, responsive to the data of amplitude of vibration $A(\omega_s)$ for varied drive frequency $\omega_s$, fits this data to the resonance function $$A(\omega_S) = \frac{A_0}{\sqrt{(\omega_S - \omega_{00})^2 + 4\omega_S^2 \gamma^2}} \quad (3)$$

so as to determine $\omega_{00}$ and $\gamma$, where $\gamma$ is the damping coefficient. The function defined in equation (3) is also referred to as the Lorentzian function. The analyzer 150 determines the resonant frequency $\omega_0$ of the sample R by the relation $\omega_0=(\omega_{00}^2-2\gamma^2)^{1/2}\approx\omega_{00}-(\gamma^2/\omega_{00})$. Optionally, the analyzer 150 determines the coefficient $A_0$.

The analyzer 150 also determines the mode n of flexural vibration. The above equations apply for any mode n of flexural vibration (n=1 designates a fundamental, n=2 a first overtone, etc.). The notation used herein is that:

$A_0 \rightarrow A_{o,n}$ ;

$\omega_{00} \rightarrow \omega_{00,n}$; and $\omega_0 \rightarrow \omega_{0,n}$.

With these substitutions, the resonance function of Equation (3) becomes:

$$A(\omega_S) = \frac{A_{0,n}}{\sqrt{(\omega_S-\omega_{00,n})^2 + 4\omega_S^2\gamma^2}} \tag{3'}$$

and $\omega_{0,n}=(\omega_{00,n}^2-2\gamma^2)^{1/2}\approx\omega_{00,n}-(\gamma^2/\omega_{00,n})$.

An exemplary method of determining the mode n of flexural vibration is to vary the drive frequency $\omega_s$ by a wide range, say, tenfold, so as to determine two resonant frequencies $\omega_{0,n1}$ and $\omega_{0,n2}$, and then determine their ratio. The resonant frequencies $\omega_{0,n}$ are of fixed and known ratios and so comparison of $\omega_{0,n1}$ and $\omega_{0,n2}$ with the known ratios would establish the values of $n_1$ and $n_2$. For example, for vibration of a reed clamped at one end and free to vibrate at the other end, $(\omega_{0,2})/(\omega_{0,1})\approx 6.267$; $(\omega_{0,3})/(\omega_{0,1})\approx 17.548$; and for large values of n, $(\omega_{0,n})/(\omega_{0,1})\approx[(n-\frac{1}{2})/0.597]^2$. If $(\omega_{0,n2})/(\omega_{0,n1})$ were measured as 2.800, then $n_1$ and $n_2$ are seen to be $n_1=2$ and $n_2=3$.

The analyzer 150 produces an output signal $S_o$ indicative of the resonant frequency $\omega_{0,n}$ and the mode n of flexural vibration. Although FIG. 1 shows vibration of a reed clamped at one end and free to vibrate at the other end, this invention applies to any mode of flexural vibration for a sample appropriately mounted, driven, and detected by appropriate detection mechanisms.

A homogeneous, uniform dc magnetic field H is then applied to the sample by a device 157, such as a superconductor magnet. This magnetic field H has a component in the selected plane of vibration. For example, for vibration in the plane of FIG. 1, the applied magnetic field H has a vertical component in this plane. The resonant frequency of the sample R in the selected plane of vibration is then determined in the presence of the applied magnetic field H by the exemplary technique described above. This resonant frequency will typically be close to the resonant frequency $\omega_{0,n}$ in zero field. More specifically, the resonant frequency $\omega_{0H,n}$ of the same mode of flexural vibration in the same plane is determined in the presence of the applied magnetic field H and output as signal $S_H$. As discussed further below, the anisotropy of the magnetic susceptibility $\chi$ of the sample R is determined based on the output signals $S_o$ and $S_H$ and based on the magnitude of the magnetic field H in the plane of flexural vibration. As shown in FIG. 1, this determination may be considered as performed by apparatus 160, an output analyzer which outputs the anisotropy of the magnetic susceptibility $\chi$ of the sample R as anisotropic susceptibility signal $S_\chi$. The susceptibility signal $S_\chi$ is functionally dependent on one or more linear combinations of the susceptibility components of the susceptibility tensor $\chi$. As discussed further below, this susceptibility signal $S_\chi$ is preferably indicative of the difference between the longitudinal and transverse tensor components.

Figure 3:
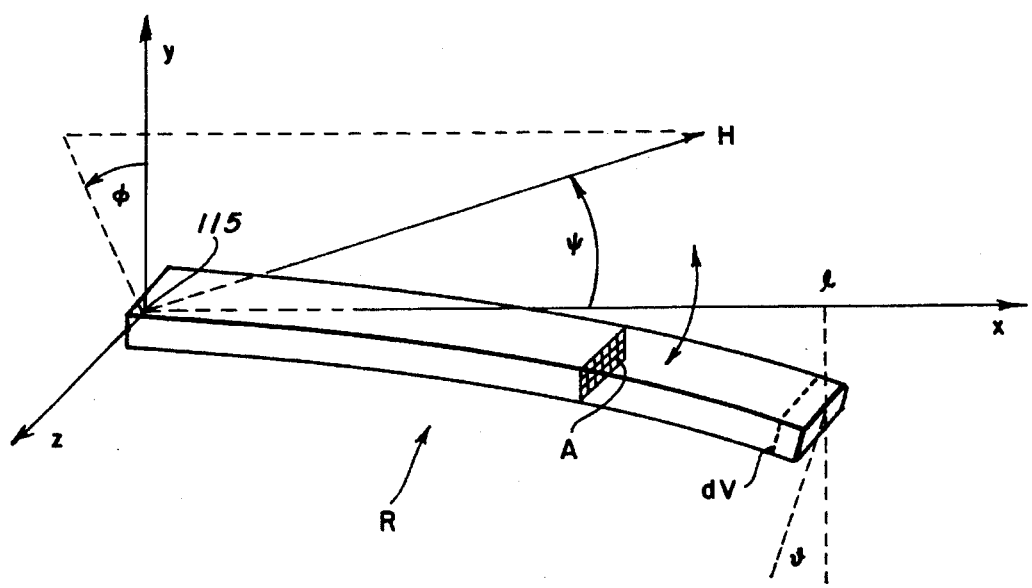
FIG. 3 shows in 3-dimensional view the physical arrangement of the vibrating sample in the laboratory frame of reference.

Referring now to FIG. 3, the reed R is of length 1 and uniform cross-sectional area A. Exemplary dimensions of the sample R are length 1 in the range from about 0.7 millimeters (mm) to about 2 centimeters (cm) and cross sectional area A in the range from about 100 square micrometers ($\mu m^2$) to about 2000 $\mu m^2$ but the invention is not limited to samples S within such a range. The cross section with area A can be circular (for example, copper wire with 51 $\mu m$ diameter) or rectangular (for example, GY-70 approximately 8×12 $\mu m^2$ or $NbSe_3$ with thickness of 10–20 $\mu m$ and width of 60 $\mu m$ or more) or any other shape for which the radius gyration of the sample's cross section can be determined. The reed R is mounted as a cantilever clamped at one end 115 and oriented with its length along the x direction. Vibration is taken to lie in the x-y plane. When the reed deflects from its equilibrium position, a volume element of the reed dV=A.dx may be tilted in the x-y plane from the equilibrium orientation. The tilt of volume element dV is measured by the angle $\theta$. Although this volume element dV is depicted as being at the end of the reed R away from the clamped end 115, volume element dV is a general volume element at an arbitrary position along the length, i.e., $0\leq x\leq 1$. The angle $\psi$ measures the azimuthal angle with respect to x of the applied magnetic field H projection in the x-y plane. $\phi$ is the polar angle with respect to y of the projection of H in the y-z plane.

A classical treatment of the vibrating reed in the absence of a magnetic field is given in P.M. Morse, "Vibration and Sound," (AIP New York, 1976) pp 151 ff As shown therein, the , mechanically resonant frequency of vibration of a given mode of the reed R in zero field is given by:

$$\omega_{0,n} = \left(\frac{\pi\beta_n}{1}\right)^2 \sqrt{\frac{\kappa^2 Y}{\rho}}, \tag{4}$$

where $\kappa$ is the radius of gyration of the reed's cross section, $\rho$ is its density, Y its longitudinal Young's modulus, and $\beta_n$ a constant determined by the boundary conditions of the vibration and the mode n of flexural vibration. The values for $\kappa$, $\rho$, Y and $\beta_n$ are readily determined. See, R. L. Jacobsen et ano, "Vibrating-Reed Dynamics in a Magnetic Field," Phys Rev Lett. 73, 348 (1994), which article is incorporated herein by reference. The resonant frequency $\omega_{0,n}$ in zero field is measured as discussed above.

Upon application of a magnetic field H to a sample R with anisotropic volume magnetic susceptibility tensor $\chi$, the resonant frequency for the n-th mode changes as described below.

A uniform magnetic field H applied to the reed R will induce a magnetization M as described by equation (2). During vibration, the reed is not usually straight, and thus the relative orientation of H with respect to the reed varies with position on the reed. Any given volume element dV inclined at an angle $\theta$ in the x-y plane in the laboratory reference frame appears to experience a field rotated by $-\theta$ in the reference frame of the reed S. Acting first on the vector H with the appropriate rotation matrix, the vector magnetization M can be expressed in terms of the susceptibility tensor components as a column vector:

$$\vec{M}(\theta) = H \begin{bmatrix} \chi_{xx}(\cos\psi\cos\theta - \sin\psi\cos\theta\sin\theta) + \chi_{xy}(\cos\psi\sin\theta + \sin\psi\cos\phi\cos\theta) + \chi_{xz}\sin\psi\sin\phi \\ \chi_{xy}(\cos\psi\cos\theta - \sin\psi\cos\theta\sin\theta) + \chi_{yy}(\cos\psi\sin\theta + \sin\psi\cos\phi\cos\theta) + \chi_{yz}\sin\psi\sin\phi \\ \chi_{xz}(\cos\psi\cos\theta - \sin\psi\cos\theta\sin\theta) + \chi_{zy}(\cos\psi\sin\theta + \sin\psi\cos\phi\cos\theta) + \chi_{zz}\sin\psi\sin\phi \end{bmatrix}, \quad (5)$$

where H is the magnitude of the applied magnetic field H.

The free-energy density associated with M is then given by $$\mathfrak{I}_M = -\frac{\mu_0}{2} \vec{M} \cdot \vec{H}, \quad (6)$$

where $\mu_0$ is the magnetic permeability of free space. For the simple case of a uniaxial crystal with its axis along x (i.e., $\chi_{yy}=\chi_{zz}=\chi_T$ (the transverse component), $\chi_{xx}=\chi_L$ (the longitudinal component), all other components $\chi_{ij}=0$), and H applied both transversely and in the plane of vibration ($\psi=90°$, $\phi=0°$), the energy is $$\mathfrak{I}_M = -\frac{\mu_0}{2} H^2[\chi_L + (\chi_T - \chi_L)\cos^2\theta]. \quad (7)$$

This illustrates the point that the anisotropy of the susceptibility, ($\chi_T-\chi_L$) in this case, causes the free energy of the element to depend on its orientation relative to the field: it varies as θ is varied. In contrast, if the susceptibility were isotropic, i.e., if $\chi_T=\chi_L$, then $\mathfrak{I}_M$ would be constant as θ were varied.

Because the free energy $\mathfrak{I}_M$ has an angular dependence, a given element will experience a torque $\tau_M$ equal to $-(d\mathfrak{I}_M/d\theta)dV$. In any reasonable vibrating-reed system, θ is always small. Expanding the torque out to second order terms in θ yields the approximation:

$$\tau_M = \mu_0 H^2\, dV\, [(-\chi_{xx}csc + \chi_{yy}csc + \chi_{xy}\eta + \chi_{yz}css - \chi_{xz}sscs) + \quad (8)$$

$$\theta \cdot (-\chi_{xx}\eta + \chi_{yy}\eta - 4\chi_{yy}csc - \chi_{yz}sscs - \chi_{xz}css) +$$

$$\theta^2 \cdot (2\chi_{xx}csc - 2\chi_{yy}csc - 2\chi_{xy}\eta - \tfrac{1}{2}\chi_{yz}css + \tfrac{1}{2}\chi_{xz}sscs)],$$

where:

csc=cos ψ·sin ψ·cos φ;
css=cos ψ·sin ψ·sin φ;
sscs=sin²ψ·cos φ·sin φ; and
η=cos²ψ−sin²ψ·cos²φ.

If $\chi_{xx}$ and $\chi_{yy}$ were equal, and if the off-diagonal elements were zero, then the torque $\tau_M=0$. In general, we further simplify equation (8) as:

$$\tau_M = \mu_0 H^2 dV[\varsigma + \zeta\theta + \xi\theta^2], \quad (9)$$

where $$\varsigma = -\chi_{xx}csc + \chi_{yy}csc + \chi_{xy}\eta + \chi_{yz}css - \chi_{xz}sscs, \quad (10)$$

$$\zeta = -\chi_{xx}\eta + \chi_{yy}\eta - 4\chi_{xy}csc - \chi_{yz}sscs - \chi_{xz}css, \quad (11)$$

and $$\xi = 2\chi_{xx}csc - 2\chi_{yy}scs - 2\chi_{xy}\eta - \tfrac{1}{2}\chi_{yz}css + \tfrac{1}{2}\chi_{yz}sscs. \quad (12)$$

Figure 4:
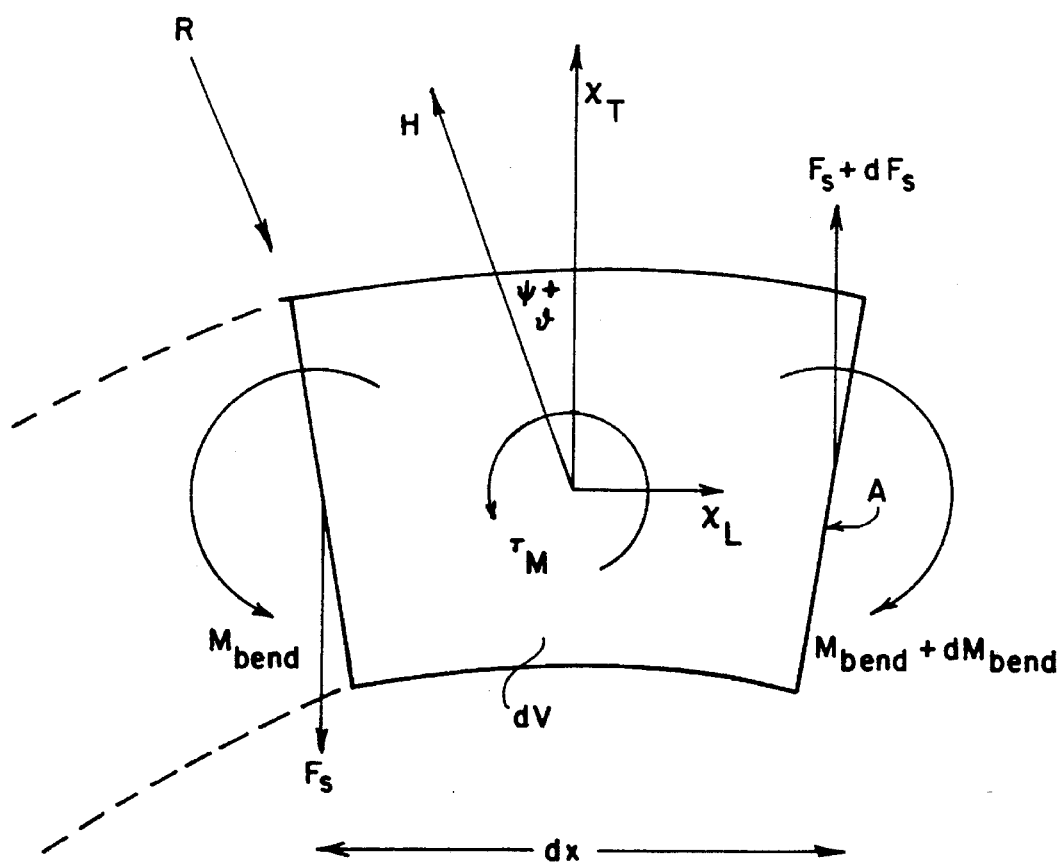
FIG. 4 shows in cross-sectional view a volume element of the vibrating sample in the sample's frame of reference.

Referring now to FIG. 4, the volume element dV is acted on by various forces and torques causing its rotation and bending. $M_{bend}$ is the bending moment of the reed, and $$M_{bend} = -YA\kappa^2(d^2y/dx^2). \quad (13)$$

$\tau_M$ is the torque from the magnetic interaction described above in equation (9). $F_s$ is the shearing force across the volume element dV. For the volume element dV to be in equilibrium, the torques acting on it must balance, and so $$F_s dx = dM_{bend} - \tau_M = \frac{\delta M_{bend}}{\delta x} \cdot dx - \tau_M. \quad (14)$$

Using equation (9) and making the small-angle substitution θ→dy/dx gives an expression for the shearing force:

$$F_S = -YA\kappa^2 \frac{d^3y}{dx^3} - A\mu_0 H^2\left[\varsigma + \zeta\frac{dy}{dx} + \xi\left(\frac{dy}{dx}\right)^2\right]. \quad (15)$$

The net force on the volume element dV is the difference $dF_s$ in this shearing force along the length. By Newton's second law of motion, and $$dF_S = m\frac{d^2y}{dt^2} = A \cdot dx \cdot \rho\, \frac{d^2y}{dt^2}, \quad (16)$$

and $$\frac{dF_S}{dx} = -YA\kappa^2\frac{d^4y}{dx^4} - \quad (17)$$

$$A\mu_0 H^2\left(\zeta\frac{d^2y}{dx^2} + 2\xi\frac{dy}{dx} \cdot \frac{d^2y}{dx^2}\right) = A\rho\frac{d^2y}{dt^2},$$

resulting in the equation of motion:

$$\frac{d^4y}{dx^4} + \frac{\mu_0 H^2}{Y\kappa^2}\left(\zeta + 2\xi\frac{dy}{dx}\right)\frac{d^2y}{dx^2} = \frac{-\rho}{Y\kappa^2}\,\frac{d^2y}{dt^2}. \quad (18)$$

This equation of motion is nonlinear because of the (dy/dx) ($d^2y/dx^2$) term. However, for small vibrations, dy/dx<<1, and it is rare for $|\zeta|<<|\xi|$. Thus, the nonlinear term can be ignored and will not be considered any further herein. Equation (18) thus becomes:

$$\frac{d^4y}{dx^4} + \frac{\mu_0 H^2 \zeta}{Y\kappa^2} \cdot \frac{d^2y}{dx^2} = \frac{-\rho}{Y\kappa^2}\,\frac{d^2y}{dt^2}. \quad (19)$$

separating variables into y(x,t)= Y(x) T(t), and assuming a time dependence of T(t)=$e^{i\omega St}$, the spatial part of the equation becomes $$\left(\frac{d^4}{dx^4} + \frac{\mu_0 H^2 \zeta}{Y\kappa^2} \cdot \frac{d^2}{dx^2} - \frac{\rho\omega^2}{Y\kappa^2}\right)(x) = 0. \quad (20)$$

The second order term $(\mu_0 H^2 \zeta)/(Y\kappa^2)$ ($d^2/Y/dx^2$) has arisen as a result of the interaction of the magnetic field with the anisotropic magnetic susceptibility. In zero field, equation (20) can readily be solved. The unperturbed eigenfrequencies $\omega_{0,n}$ for a reed clamped and one end and free to vibrate at the other end are expressed above in equation (4). The unperturbed eigenfunctions are:

$$Y_n(x) = a_n\left[\cosh\left(\frac{\pi\beta_n x}{1}\right) - \cos\left(\frac{\pi\beta_n x}{1}\right)\right] + \quad (21)$$

$$b_n\left[\sinh\left(\frac{\pi\beta_n x}{1}\right) - \sin\left(\frac{\pi\beta_n x}{1}\right)\right],$$

where $a_n$ is arbitrary, $$b_n = -a_n\left[\frac{\cosh(\pi\beta_n) + \cos(\pi\beta_n)}{\sinh(\pi\beta_n) + \sin(\pi\beta_n)}\right], \quad (22)$$

and $\beta_n$ are solutions to the transcendental equation $$\cosh(\pi\beta_n)\cos(\pi\beta_n) = -1, \quad (23)$$

Equation (20) is a fourth-order, ordinary, linear, homogeneous differential equation with constant coefficients, and solutions to it can be calculated to arbitrarily precise accuracy by standard numerical techniques. Another approach is to use perturbation techniques as described below. Regardless of the approach used once the solution for $y(x)$ is obtained, equation (20) is used to determine $\zeta$. For the simple case of a uniaxial crystal with its axis along x (i.e., $\chi_{yy}=\chi_{zz}=\chi_T$ (the transverse component), $\chi_{xx}=\chi_L$ (the longitudinal component), all other components $\chi_{ij}=0$ equation (11) reduces to $$\zeta = (\chi_T - \chi_L)\eta. \tag{24}$$

$\eta$ is determined by the orientation of the field H relative to the sample and the sample's plane of flexural vibration, and so anisotropy of the susceptibility $\chi_T-\chi_L$ is readily determined from equation (24) once $\zeta$ is known.

As to the perturbation approach, equation (20) is rewritten as $$[\mathcal{H} + \mathcal{P}] \, y(x) = [\omega_{0,n}^2 + \delta(\omega_n^2)] \, y(x), \tag{25}$$

where $\mathcal{H}$ is an operator describing the vibrating reed in zero field, and $\mathcal{P}$ is the perturbation operator arising from the applied magnetic field giving rise to the small correction $\delta((\omega_n)^2)$. From equation (20), the operators $\mathcal{H}$ and $\mathcal{P}$ are:

$$\mathcal{H} = \frac{Y\kappa^2}{\rho} \cdot \frac{d^4}{dx^4} \; ; \; \mathcal{P} = \frac{\mu_0 H^2 \zeta}{\rho} \cdot \frac{d^2}{dx^2}. \tag{26}$$

The first order correction to $\omega_{0,n}^2$ is then given by the expectation value of $\mathcal{P}$ acting on the eigenfunction of the unperturbed system, $y_n(x)$, where the expectation value is given by:

$$\delta(\omega_n^2) = \frac{\int_0^1 y_n(x) \, \mathcal{P} \, y_n(x) dx}{\int_0^1 y_n(x) \, y_n(x) dx}. \tag{27}$$

Carrying out the integration of equation (27), dividing through by $\omega_{0,n}^2$, and substituting the result of equation (4) gives a fractional change to the eigenfrequency of:

$$\frac{\delta(\omega_n^2)}{\omega_{0,n}^2} = M_n \frac{\mu_0 H^2 l^2}{Y\kappa^2} \zeta, \tag{28}$$

where the values of $M_n$ are given, to the first order, by the expression:

$$M_n = \frac{l^2}{(\pi\beta_n)^4} \frac{\int_0^1 y_n(x)(d^2/dx^2) \, y_n(x)dx}{\int_0^1 y_n(x) \, y_n(x)dx}. \tag{29}$$

Values of $M_n$ are tabulated in R. L. Jacobsen et ano, "Vibrating-Reed Dynamics in a Magnetic Field," Phys. Rev. Lett. 73, 348, supra. $M_n$, like $\beta_n$, is a numerical factor determined by the mode under investigation. Determination of $\beta_n$ or $M_n$ requires four boundary conditions, and each boundary condition can be specified as a value for $y_n$ or any of its first three derivatives at a point on the reed.

Since the perturbation $\delta(\omega_{0,n}^2)/(\omega_{0,n}^2)$ is measured by the techniques discussed above, and all constants are known, equation (28) is used to determine $\zeta$. For the simple case of a uniaxial crystal with its axis along x (i.e., $\chi_{yy}=\chi_{zz}=\chi_T$ (the transverse component), $\chi_{xx}=\chi_L$ (the longitudinal component), all other components $\chi_{ij}=0$) equation (11) reduces to equation (24), and the anisotropy of the susceptibility $\chi_T-\chi_L$ is readily determined from equation (24).

Other techniques besides determining $\zeta$ from equation (28), and besides perturbation techniques and numerical techniques may be equally effectively used to determine the anisotropy of the susceptibility.

The present invention may also be practiced to determine the anisotropy of the differential susceptibility of a sample. As noted above, for diamagnetic, paramagnetic and antiferromagnetic material, the anisotropy of the differential susceptibility has the same value as the anisotropy of the susceptibility. In order to measure the anisotropy of the differential susceptibility, the resonant frequency for flexural vibration is determined in the presence of at least a first and then a second magnetic field having differing magnitudes in the selected plane of vibration. The anisotropy of the differential susceptibility is then determined based on a comparison of the resonant frequencies for the at least two differing magnetic fields. If one of the magnetic fields is zero field, this situation reduces to the above described system for determining the anisotropy of the susceptibility of a sample. Furthermore, for diamagnetic, paramagnetic and antiferromagnetic material, the anisotropy of the differential susceptibility has the same value as the anisotropy of the susceptibility.

The present invention may also be used to measure the anisotropy of the susceptibility or the anisotropy of the differential susceptibility for other types of materials having magnetic properties, such as samples R containing ferromagnetic material in which the ferromagnetic material makes up a small proportion of the sample R. An example of such a sample R is a thin film ferromagnetic material on a substrate which does not have ferromagnetic properties.

The foregoing descriptions of the preferred embodiments are intended to be illustrative and not limiting. It will be appreciated that numerous modifications and variations can be made without departing from the spirit or scope of the present invention.

What is claimed is:

1. A method for determining the anisotropy of the magnetic susceptibility of a sample comprising the steps:

(a) determining the resonant frequency of the sample in substantially zero magnetic field, the resonant frequency being for flexure vibration in a selected plane of vibration;

(b) applying a uniform dc magnetic field to the sample, the magnetic field having a component in the selected plane of vibration;

(c) determining the resonant frequency of the sample in the presence of the magnetic field applied in step (b), the resonant frequency being for flexure vibration in the selected plane; and (d) determining the anisotropy of the magnetic susceptibility of the sample, said determining step being dependent on the amplitude of the magnetic field component applied in step (b) and on the resonant frequencies determined in steps (a) and (c).

2. The method of claim 1, said determining resonant frequency steps (a) and (c) each being responsive to the capacitance between the sample and a fixed member.

3. The method of claim 1, further comprising determining the proportional difference between the squares of the resonant frequencies determined in steps (a) and (c);

said determining step (d) being dependent on the proportional difference between the squares of the resonant frequencies determined in steps (a) and (c).

4. An apparatus for determining the anisotropy of the magnetic susceptibility of a sample comprising:

(a) means for determining the resonant frequency of the sample in substantially zero magnetic field, the resonant frequency being for flexure vibration in a selected plane of vibration;

(b) means for applying a uniform dc magnetic field to the sample, the magnetic field having a component in the selected plane of vibration;

(c) means for determining the resonant frequency of the sample in the presence of the magnetic field applied by means (b), the resonant frequency being for flexure vibration in the selected plane; and (d) means for determining the anisotropy of the magnetic susceptibility of the sample, said determining means being dependent on the amplitude of the magnetic field component applied by means (b) and on the resonant frequencies determined by means (a) and (c).

5. The apparatus of claim 4, said determining resonant frequency means (a) and (c) each being responsive to the capacitance between the sample and a fixed member.

6. The apparatus of claim 4, further comprising means determining the proportional difference between the squares of the resonant frequencies determined in steps (a) and (c);

said determining means (d) being dependent on the proportional difference between the squares of the resonant frequencies determined by means (a) and (c).

7. A method for determining the anisotropy of the differential magnetic susceptibility of a sample comprising the steps:

(a) applying a first uniform dc magnetic field to the sample, the first magnetic field having a component in a selected plane of vibration;

(b) determining the resonant frequency of the sample in the presence of the first magnetic field applied in step (a), the resonant frequency being for flexure vibration in the selected plane;

(c) applying a second uniform dc magnetic field to the sample, the second magnetic field having a component in the selected plane of vibration wherein said component of said second dc field is different from said component of said first dc field;

(d) determining the resonant frequency of the sample in the presence of the second magnetic field applied in step (c), the resonant frequency being for flexure vibration in the selected plane; and (e) determining the anisotropy of the magnetic susceptibility of the sample, said determining step being dependent on the amplitudes of the first and second magnetic field components applied in steps (a) and (c), and on the resonant frequencies determined in steps (b) and (d).

8. The method of claim 7, said determining resonant frequency steps (b) and (d) each being responsive to the capacitance between the sample and a fixed member.

9. An apparatus for determining the anisotropy of the differential magnetic susceptibility of a sample comprising:

(a) means for applying a first uniform dc magnetic field to the sample, the first magnetic field having a component in a selected plane of vibration;

(b) means for determining the resonant frequency of the sample in the presence of the first magnetic field applied by means (a), the resonant frequency being for flexure vibration in the selected plane;

(c) means for applying a second uniform dc magnetic field to the sample, the second magnetic field having a component in the selected plane of vibration wherein said component of said dc field is different from said component of said first dc field;

(d) means for determining the resonant frequency of the sample in the presence of the second magnetic field applied by means (c), the resonant frequency being for flexure vibration in the selected plane; and (e) means for determining the anisotropy of the differential magnetic susceptibility of the sample, said determining means being dependent on the amplitudes of the first and second magnetic field components applied by means (a) and (c), and on the resonant frequencies determined by means (b) and (d).

10. The apparatus of claim 9, said determining resonant frequency means (b) and (d) each being responsive to the capacitance between the sample and a fixed member.

* * * * *